US00PP30086P3

(12) United States Plant Patent
Austin

(10) Patent No.: US PP30,086 P3
(45) Date of Patent: Jan. 15, 2019

(54) ***ROSA HYBRIDA* SHRUB NAMED 'AUSOUTCRY'**

(50) Latin Name: *Rosa hybrida*
Varietal Denomination: AUSoutcry

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 227 days.

(21) Appl. No.: 14/999,440

(22) Filed: May 4, 2016

(65) Prior Publication Data

US 2017/0079171 P1 Mar. 16, 2017

(30) Foreign Application Priority Data

Sep. 15, 2015 (QZ) ..... PBR 2015/2228

(51) Int. Cl.
*A01H 5/02* (2018.01)

(52) U.S. Cl.
USPC ..... Plt./107

(58) Field of Classification Search
USPC ..... Plt./107
See application file for complete search history.

*Primary Examiner* — Keith O. Robinson
(74) *Attorney, Agent, or Firm* — KPPB LLP

(57) ABSTRACT

A variety of rose plant of the shrub class, named 'AUSoutrcry'. The 'AUSoutcry' is a variety of rose having pink buds which open to many-petalled, incurved, cupped blooms with a strong, warm myrrh fragrance. The blooms are a rich glowing pink at the centre, which become paler towards the edges.

1 Drawing Sheet

Classification: The present invention relates to a new *Rosa hybrida* shrub of the market class 'English Rose'.

Variety denomination: The new plant has the varietal denomination 'AUSoutcry'.

CROSS-REFERENCE TO RELATED APPLICATION

The present application claims priority to European CPVO 2015/2228, filed Sep. 24, 2015.

ORIGIN OF INVENTION

This invention relates to a new and distinct variety of shrub rose plant named 'AUSoutcry', which was originated from the cross-pollination of the two 'unnamed' and unpatented seedlings of *Rosa hybrida.*

BACKGROUND OF THE INVENTION

The primary objective of this breeding was to produce a rose variety having pink buds which open to many-petalled, incurved, cupped blooms with a strong, warm myrrh fragrance.

SUMMARY OF THE INVENTION

Among the features which distinguish the new variety from others presently available and commercial rose cultivars known to the inventor is the following combination of characteristics: blooms having many petals pink in color that are incurved and cupped; a strong and warm myrrh fragrance; where the bloom is paler towards its outer petals; and where stamens are not evident in the center of the bloom.

Asexual reproduction of the new variety by budding as performed at Bowling Green Lane in Albrighton, Britain shows that the foregoing and other distinguishing characteristics come true to form and are established and transmitted through succeeding asexual propagations. 'AUSoutcry' may be asexually propagated by budding. The budding successfully occurred on the unpatented plant/rootstock *Rosa dumetorum* 'Laxa' for the observed plants.

COMPARISON WITH PARENTS

The maternal and paternal parents of 'AUSoutcry' are two unnamed seedlings. The new rose may be distinguished from its maternal parent, by the following combination of characteristics: the maternal parent has more sprawling, uneven growth habit and produces fewer petals. The new rose may be distinguished from its pollen parent, by the following combination of characteristics: the paternal parent has a shorter, although upright, growth habit and produces fewer petals.

COMPARISON WITH THE CLOSEST COMMERCIALLY AVAILABLE CULTIVAR

The closest commercially available cultivar to the new variety is the 'AUSmixture' (U.S. Plant Pat. No. 27,365). The new rose may be distinguished from 'AUSmixture' because the blooms of the prior cultivar are quartered rosettes with approximately 90 petals, whereas the blooms of 'AUSoutcry' are incurved cups with approximately 160 petals. 'AUSmixture' is a well-balanced shrub growing approximately 105 cm×90 cm, whereas 'AUSoutcry' is vigorous and upright, growing approximately to 150 cm×90 cm. The new shoots and foliage of 'AUSmixture' are not as red as the new growth on 'AUSoutcry'. Finally, 'AUSoutcry' has the unusual characteristic of no stamens being evident, whereas there are stamens evident on 'AUSmixture'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSoutcry' specimens were made at the nursery at David Austin Roses Limited in Albrighton, Wolverhampton, United Kingdom. The following description is of a 5 year-old rose plant of the new variety grown in a garden environment in Albrighton, Britain in the month of June. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

- *Size*.—About 2.6 cm long and 3.0 cm in diameter when the petals start to unfurl.
- *Form*.—The bud form is broad based.
- *Color*.—When sepals first divide, the bud color is RHS 47C (red group). When half blown, the upper sides of the petals are RHS 65B (red-purple group), and the lower sides of the petals are RHS 65B (red-purple group).
- *Calyx*.—Shape: opens to a star shape, with the sepals finally folding back against the stems. Length: 7.5 cm. Diameter: 7.5 cm.
- *Sepals*.—Arrangement: Regularly arranged. Color: Upper Surface: RHS 139C (green group). Lower Surface: RHS 143C (green group). Extension: Weak. Length: 3.5 cm. Width: 1.3 cm. Shape: Lanceolate. Surface texture: Upper Surface: Downy. Lower Surface: Glandular. Number: There are NO appendaged sepals, and 5 unappendaged sepals with glandular edges.
- *Receptacles*.—Color: RHS 144A (yellow-green group) with RHS 178B (greyed-red group). Shape: funnel. Size: broad, about 1.0 cm long×1.6 cm wide. Surface: Smooth.
- *Peduncle*.—Length: long, averaging about 7 cm. Surface: smooth. Color: RHS 144A (yellow-green group) with RHS 178B (greyed-red group). Strength: Strong.

Blooms:

- *Size*.—Large, average open diameter is about 9 cm.
- *Borne*.—Several together in clusters of 4-14 with clusters having a rounded shape.
- *Stems*.—Strength: strong, average length is about 20 cm. Diameter: 4 mm.
- *Form*.—When first open, bloom is cupped. Permanence of bloom: outer petals curl back.

Petalage: Number of petals under normal conditions: 160.

- *Type*.—Double.
- *Color*.—The upper sides of the petals are RHS 65C (red-purple group). The reverse sides of the petals are RHS 65C (red-purple group). The base of the petals has a yellow spot, RHS 9C (yellow group) of medium size.
- *Variegations*.—None.
- *Discoloration*.—The general tonality at the end of the first day is RHS 65C (red-purple group), and at the end of the third day is RHS 65C (red-purple group).
- *Fragrance*.—Strong. Character of fragrance: myrrh.

Petals:

- *Texture*.—Whole of petal: Smooth. Upper surface: Smooth.
- *Size*.—Width: 4.5 cm. Length: 5.0 cm.
- *Surface*.—Smooth.
- *Shape*.—Obovate.
- *Margin*.—Slightly frilled some petals, but with entire margins.
- *Apex shape*.—Rounded.
- *Base shape*.—Acute.
- *Form*.—Incurved.
- *Arrangement*.—Imbricated.
- *Petaloids*.—Number: NONE.
- *Persistence*.—Petals drop off cleanly before drying.
- *Lastingness*.—On the plant: fair about 6 days. As a cut flower: not tested.

Reproductive parts:

- *Stamens*.—Number: NONE evident.
- *Anthers*.—N/A.
- *Filaments*.—N/A.
- *Pollen*.—N/A.
- *Pistils*.—Number: 40. Length: 11-12 mm.
- *Styles*.—Color: RHS 51B (red group) with RHS 196A (greyed-green group). Length: 9 mm.
- *Stigmas*.—Color: RHS 162A (greyed-yellow group). Length: 0.5-2 mm.
- *Hips*.—NONE Observed.

PLANT CHARACTERISTICS

Plant form: Shrub.

Plant growth: Vigorous.

Age to maturity: 2 years.

Mature plant: Height: 150 cm. Width: 90 cm.

Rootstock: 'Dr. Huey' (unpatented) in the U.S. and *Rosa dumetorum* 'Laxa' (unpatented) for the observed plants in the UK.

Foliage:

- *Number*.—Leaflets on normal mid-stem leaves is: 5 (including terminal leaflet).
- *Size*.—Large, about 19 cm long×13 cm wide.
- *Quantity*.—Abundant. Number of leaves per flowering stem is: 10.
- *Color*.—New foliage: Upper side: RHS 59A (red-purple group). Lower side: RHS 59A (red-purple group). Old foliage: Upper side: RHS 147A (yellow-green group). Lower side: RHS 147B (yellow-green group).

Leaflets:

- *Size*.—About 6-7 cm long×4.5 cm wide.
- *Shape*.—Oval.

*Base shape*.—Rounded.
*Apex shape*.—Acuminate.
*Texture*.—Upper side: Glossy.
*Glossiness*.—Strong.
*Edge*.—Serrated.
*Serrations*.—Single.
*Petiole*.—Color: RHS 183A (greyed-purple group). Length: 5 cm. Width: 2 mm. Surface Texture: Glandular.
*Petiole rachis*.—Color: RHS 183B (greyed-purple group). Underside: with prickles.
*Stipules*.—Length: 2.5 cm, glandular. Color: RHS 183B (greyed-purple group).
*Auricle*.—Shape: Lanceolate. Length: 9 mm. Width: 2.5 mm. Color: RHS 183B (greyed-purple group).
*Vein color*.—Color: Upper: RHS 147A (yellow-green group). Lower: RHS 147B (yellow-green group).
*Venation pattern*.—Reticulate.

Wood:
*New wood*.—Color: RHS 59A (red-purple group). Bark: Smooth.
*Old wood*.—Color: RHS 147A (yellow-green group). Bark: Smooth.

Branching habit:
*Number*.—9.
*Branching dimension*.—Length: 65 cm. Diameter: 9 mm.

Stems:
*Mature stem*.—Length: 125 cm. Diameter: 9 mm.
*Internode distance*.—7-15 cm. The above measurements are all variable, depending on growing conditions in a season.
*Stem pubescence present*.—No.

Prickles:
*Quantity*.—On main canes from base: Few. Number per stem length: 4 per 10 cm. On laterals from main canes: NONE. Number per stem length: 0 per 10 cm.
*Form*.—Deep concave.
*Length*.—6 mm.
*Color when young*.—RHS 183B (greyed-purple group).
*Color when mature*.—RHS 199C (greyed-brown group).

Small prickles:
*Quantity*.—Main stalk: None. Laterals: None.

Disease resistance:
*Powdery mildew*.—Caused by the fungus *Sphaerotheca pannosa*: Resistant.
*Downy mildew*.—Caused by species of the fungi *Peronospora, Bremia* and *Plasmopara*: Resistant.
*Blackspot*.—Caused by the fungus: *Diplocarpon*: Resistant.
*Rust*.—Cause by the fungus *Phragmidium*, including, *P. tuberculatum* and *P. mucronatum*: Resistant.

Pest resistance: Not tested.
Winter hardiness: Not tested.
Growing conditions: Normal garden conditions.

What is claimed is:

1. A new and distinct variety of rose plant of the shrub class, substantially as herein shown and described.

* * * * *

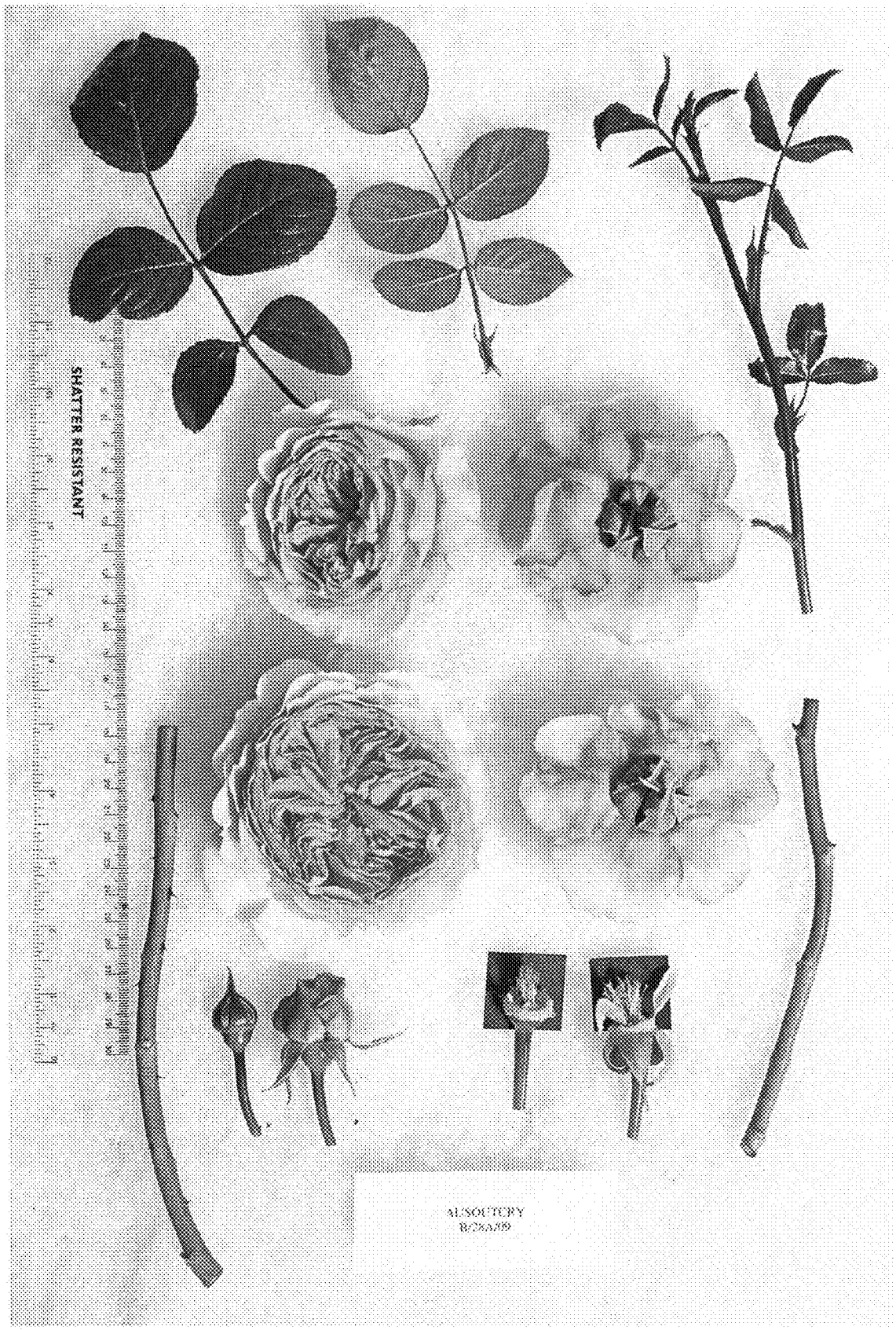
SHATTER RESISTANT
ALSOUTCPY
B/28/19